United States Patent
Zachwieja et al.

(10) Patent No.: US 10,130,607 B2
(45) Date of Patent: *Nov. 20, 2018

(54) METHODS OF REDUCING BLOOD LACTATE CONCENTRATION

(71) Applicant: Stokely-Van Camp, Inc., Chicago, IL (US)

(72) Inventors: Jeffrey J. Zachwieja, Algonquin, IL (US); Mark Arthur Pirner, Newtown, CT (US); JohnEric William Smith, Starkville, MS (US)

(73) Assignee: Stokely-Van Camp, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/630,794

(22) Filed: Jun. 22, 2017

(65) Prior Publication Data

US 2017/0281590 A1 Oct. 5, 2017

Related U.S. Application Data

(60) Continuation of application No. 14/954,687, filed on Nov. 30, 2015, now Pat. No. 9,693,991, which is a division of application No. 13/229,816, filed on Sep. 12, 2011, now Pat. No. 9,198,453.

(60) Provisional application No. 61/498,007, filed on Jun. 17, 2011, provisional application No. 61/383,973, filed on Sep. 17, 2010.

(51) Int. Cl.
| | | |
|---|---|---|
| *A61K 31/35* | (2006.01) | |
| *A61K 31/352* | (2006.01) | |
| *A23L 2/38* | (2006.01) | |
| *A23L 2/52* | (2006.01) | |
| *A23L 33/105* | (2016.01) | |
| *G01N 33/487* | (2006.01) | |
| *G01N 33/50* | (2006.01) | |
| *A61K 9/00* | (2006.01) | |

(52) U.S. Cl.
CPC ............. *A61K 31/352* (2013.01); *A23L 2/38* (2013.01); *A23L 2/52* (2013.01); *A23L 33/105* (2016.08); *A61K 9/0095* (2013.01); *G01N 33/48728* (2013.01); *G01N 33/5061* (2013.01); *A23V 2002/00* (2013.01)

(58) Field of Classification Search
CPC ...................................... A61K 31/35
USPC ........................................ 514/456
See application file for complete search history.

(56) References Cited

U.S. PATENT DOCUMENTS

| | | | | |
|---|---|---|---|---|
| 9,693,991 | B2 * | 7/2017 | Zachwieja | ............ A61K 31/352 |
| 2010/0196577 | A1 * | 8/2010 | Rivera | ....................... A23L 2/52 |
| | | | | 426/590 |
| 2011/0033586 | A1 * | 2/2011 | Rinaldi | .................. A23P 10/00 |
| | | | | 426/231 |

OTHER PUBLICATIONS

Tropicana, Tropicana.com, accessed Apr. 23, 2018, 1 page.
Shareholder Information Frequently Asked Questions, Pepsico.com, accessed Apr. 23, 2018, 6 pages.

* cited by examiner

*Primary Examiner* — Rei Tsang Shiao
(74) *Attorney, Agent, or Firm* — Brandon V. Zuniga; James R. Gourley; Carstens & Cahoon, LLP (57) ABSTRACT

The present invention is directed to methods for reducing blood lactate concentration during exercise, physical activity or athletic performance.

21 Claims, 5 Drawing Sheets

METHODS OF REDUCING BLOOD LACTATE CONCENTRATION

RELATED APPLICATION DATA

This application is a continuation of U.S. patent application Ser. No. 14/954,687, entitled "Methods of Reducing Blood Lactate Concentration," filed on Nov. 30, 2015, and published as US 2016/0151327 A1 on Jun. 2, 2016, which is a divisional of U.S. patent application Ser. No. 13/229,816, entitled "Methods of Reducing Blood Lactate Concentration," filed on Sep. 12, 2011, and published as US 2012/0077873 A1 on Mar. 26, 2012, which claims priority to U.S. Provisional Patent Application No. 61/383,973, entitled "Methods of Reducing Blood Lactate Concentration," filed on Sep. 17, 2010 and U.S. Provisional Patent Application No. 61/498,007, entitled "Methods of Reducing Blood Lactate Concentration," filed on Jun. 17, 2011. Furthermore, all applications and publications described in this paragraph, along with any patents granted for the applications, are expressly incorporated herein by reference in their entirety as examples.

FIELD

The present invention relates to the field of improving athletic performance by lowering blood lactate concentration and/or raising lactate threshold, i.e. maximal lactate steady state in an individual engaged in high intensity athletic activities. The present invention further relates to the field of assays, and in particular to the field of assays for determining the ability of a compound to reduce blood lactate concentration during high intensity exercise.

BACKGROUND

During exercise, lactic acid or lactate is produced in contracting skeletal muscle. Lactic acid that is not otherwise used by the cell is cleared from the cell and carried into the blood stream as lactate since hydrogen ion dissociates from lactic acid. Individuals have a resting blood lactate concentration. The more a muscle cell contracts, however, the more lactic acid or lactate is produced in the muscle cell and the more lactic acid is carried into the blood stream as lactate and dissociated hydrogen ion. When the rate of production of lactic acid exceeds the rate of lactate clearance or removal and hydrogen ion buffering capacity, blood lactate concentration increases and blood pH decreases.

The blood lactate concentration for an individual at which the individual has a reduced ability to sustain exercise intensity as manifested, for example, by fatigue is known as the lactate threshold or maximal lactate steady state. A common maximal lactate steady state in an individual is about 4 mmol blood lactate. Individuals with an ability to sustain a higher percentage of their maximum capacity for exercise before reaching maximal lactate steady state tend to be better endurance athletes. That is, an individual's ability to sustain a higher percentage of their maximum capacity for exercise before reaching maximal lactate steady state can be used to predict endurance performance.

A common method for increasing an individual's lactate threshold or for improving an individual's work output at maximal lactate steady state is through exercise training. Regular exercise training increases mitochondrial biogenesis such that the content of mitochondria is increased in muscle. Without wishing to be bound by scientific theory, a higher mitochondrial mass may lead to a lower rate of lactic acid production, an increased clearance rate of lactate (via oxidation) or both for a given level of exercise intensity. As a result, lactate threshold is effectively increased or lactate response during exercise is effectively improved, that is, the individual has the ability to exercise at a higher intensity before exceeding their maximal lactate steady state, for example before a blood lactate concentration of 4 mmol is reached.

Quercetin is a flavonol found in some fruits and vegetables. A cocktail including quercetin, green tea extract, vitamin C, vitamin E, caffeine, niacin, taurine, vitamin B6, vitamin B2, vitamin B1, and glucose was studied and reported to improve cycling time trial performance under certain conditions. However, the investigators recognized that the improved performance could not be attributed to quercetin alone. See MacRae and Mefferd, *International Journal of Sport Nutrition and Exercise Metabolism*, 2006, 16, 405-419. Quercetin has been reported to increase mouse brain and mouse muscle mitochondrial biogenesis and exercise tolerance in mice. See Davis et al., *Am. J. Physiol. Regul. Inter. Comp. Physiol.* 296: R1071-R1077 (2009). Quercetin has also been reported to increase maximal oxygen uptake and cycling performance in certain individuals. See Davis et al., *International Journal of Sport Nutrition and Exercise Metabolism*, 2009, 20, 1013. The effect of quercetin and DMSO on skeletal myogenesis from C2C12 skeletal muscle cells has been reported. See Basic Appl Myol 11 (1): 31-44 (2001). However, none of the studies demonstrated a method of reducing blood lactate concentration by administration of quercetin to an individual, methods of improving muscle cell performance in an individual by reducing blood lactate concentration, or methods of increasing the lactate threshold or the maximal lactate steady state in an individual allowing extended high intensity physical activity.

It is therefore an object of the present invention to reduce blood lactate concentration in an individual by administration of quercetin. It is a further object of the present invention to extend high intensity physical activity by reducing blood lactate concentration. It is a still further object of the present invention to create an assay for identifying compounds capable of reducing lactic acid concentrations in a muscle cell. These and other objects, features, and advantages of the invention or certain embodiments of the invention will be apparent to those skilled in the art from the following disclosure and description of exemplary embodiments.

SUMMARY

Embodiments of the present invention are directed to methods for reducing blood lactate concentration in an individual during exercise. According to this aspect of the present invention, an individual is administered quercetin according to a particular regimen prior to physical exercise. The individual then engages in physical exercise and experiences a reduction in blood lactate concentration relative to that achieved by the individual for the physical exercise without being administered quercetin. According to one aspect of this embodiment, a method of increasing exercise performance, that is, increased ability for work output at a 4 mmol blood lactate concentration, is provided by administering quercetin according to a particular regimen to an individual prior to exercise. Further, when the individual engages in exercise, blood lactate concentration is reduced at the same work output relative to exercising without being administered quercetin, and then this will lead to additional exercise time and work output before fatigue and beyond that experienced by the individual without quercetin administration. According to this aspect, administration of quercetin increases the individual's lactate threshold or the individual's maximal lactate steady state and improves tolerance for exercise as measured by increased time to fatigue for a particular physical activity or a faster time to complete a specified distance or shorter time to accumulate a specified amount of work. Additional aspects of the present disclosure are directed to the administration of quercetin during training, i.e. during physical exercise. Training may precede a particular physical event, such as a competitive physical event. According to this aspect, the administration of quercetin during physical training results in an individual experiencing a reduction in blood lactate concentration relative to that achieved by the individual for the physical exercise without being administered quercetin. According to one aspect of this embodiment, a method of increasing exercise performance, that is, increased ability for work output at a 4 mmol blood lactate concentration, is provided by administering quercetin according to a particular regimen to an individual during exercise training regimens. Further, when the individual engages in exercise, blood lactate concentration is reduced meaning a greater exercise intensity can be achieve at maximal lactate steady state after quercetin consumption thereby allowing the individual to cover a set distance more quickly or reduce the time it takes to accumulate a specified amount of work. According to an additional aspect, when the individual engages in exercise, blood lactate concentration is reduced at the same work output relative to exercising without being administered quercetin, and then this will lead to additional exercise time and work output before fatigue and beyond that experienced by the individual without quercetin administration. According to this aspect, administration of quercetin increases the individual's lactate threshold or maximal lactate steady state and improves tolerance for exercise as measured by increased time to fatigue for a particular physical activity or by a decreased time to cover a set distance or accumulate a specified amount of work.

Certain embodiments of the present invention are based on the use of a muscle cell culture assay to identify compounds that decrease lactic acid generated within a cell as a result of muscle cell contraction such as elicited by electrical stimulation while in culture or during physical exercise by an individual. According to the present invention, muscle cells engaged in repeated contraction, such as by electrical stimulation while in culture or by physical exercise, generate lactic acid or lactate. Accumulation of lactic acid or lactate within a cell beyond that in a normal resting cell can lead to muscle fatigue and/or reduced muscle cell performance. According to one aspect of the present invention, muscle cells will have increased ability, i.e. beyond a natural ability of the cell, to contract when administered quercetin in a manner to reduce lactic acid or lactate amount or concentration within a cell.

Methods of administering quercetin according to aspects of the present invention are effective when quercetin is administered directly to a muscle cell, to media surrounding a muscle cell or to an individual as a supplement, food, meal replacement bar, confectioneries, snack foods or beverage product to reduce blood lactate amount or concentration that results from contraction, such as by electrical stimulation of muscle cells in a culture or during physical exercise by the individual. According to one aspect, quercetin lowers concentration of lactic acid or lactate in muscle cells or media surrounding muscle cells. According to another aspect, quercetin lowers blood lactate amount or concentration. According to a still further aspect, quercetin inhibits or otherwise reduces the formation of lactic acid or lactate within a muscle cell. According to an even still further aspect, quercetin inhibits or otherwise reduces accumulation of lactate in blood.

According to certain aspects of the present invention, methods are provided to reduce muscle fatigue and/or loss of muscle performance by administering quercetin in a manner to lower lactic acid amount or concentration within a cell during contraction in culture or in a manner to lower blood lactate amount or concentration in an individual during exercise. The methods of the present invention include raising an individual's tolerance to exercise or capacity for intense exercise by increasing the individual's blood lactate threshold, or maximal lactate steady state by increasing the individual's exercise time to fatigue, reducing the amount of time it takes to cover a set distance or by lowering the blood lactate concentration for a given work output, by administering quercetin in a manner to lower lactic acid amount or concentration within a cell during contraction or in a manner to lower blood lactate amount or concentration in an individual during exercise for a given work output.

Lowering lactic acid or lactate within a muscle cell or blood lactate concentration increases the ability of the muscle to continually contract before fatigue and/or muscle cell failure prevents or reduces further contraction. Accordingly, certain aspects are directed to increasing the ability of a muscle cell to contract by administering quercetin to the muscle cell thereby prolonging the ability of the muscle cell to contract relative to a control muscle cell without administration of quercetin. Aspects of the present invention include preventing, reducing or otherwise delaying the onset of muscle fatigue in an individual associated with exercise by administering quercetin prior to exercise and reducing blood lactate concentration during exercise. Aspects of the present invention also include prolonging exercise time of an individual or reducing the amount of time needed to cover a specified distance by an individual by reducing muscle fatigue by administering quercetin prior to exercise and reducing blood lactate concentration during exercise. Still further aspects of the present invention include enhancing athletic performance in individuals by reducing muscle fatigue by administering quercetin prior to exercise and reducing blood lactate concentration during exercise.

Embodiments of the present invention are also directed to a muscle cell assay and to methods of using a muscle cell assay to determine the ability of a compound to prevent, reduce, inhibit or limit production of lactic acid within the muscle cell as a result of contraction. The muscle cell assay of the present invention is used to quantify the amount of lactic acid production involved in the process of muscle contraction. According to this aspect, the lactate concentration in media of a resting muscle cell culture is determined. Other muscle cells in culture are caused to contract by electrical stimulation for a period of time and at a frequency and pulse duration. Lactate concentration in the culture media from contracting cells is measured to determine the extent of lactic acid production in the active relative to unstimulated or resting muscle cells. Muscle cells are also contacted with a candidate compound and the muscle cells are caused to contract by electrical stimulation for the same period of time and at the same frequency and pulse duration. According to one embodiment, the candidate compound is quercetin. Lactate concentration in cell culture media is measured and then compared with the lactate concentration in active (without candidate compound incubation) and resting cells. If the lactate concentration is reduced in the stimulated muscle cells contacted with the candidate compound, then the compound is selected and/or identified as a compound capable of reducing muscle fatigue and/or enhancing physical performance, for example in an individual by reducing blood lactate concentration during exercise and/or increasing the blood lactate threshold of an individual for a given work output.

According to an additional aspect, muscle cells in culture are caused to contract by electrical stimulation at a frequency and pulse duration and for a period of time until the point of failure, i.e., until the muscle cells stop contracting. Lactate concentration in the culture media is then measured. Muscle cells are also contacted with a candidate compound and are caused to contract by electrical stimulation at the same frequency and pulse duration until the point of failure and the lactate concentration is measured. In a preferred embodiment, the candidate compound is quercetin. The time to failure for active cells without compound incubation is compared with the time to failure for cells contracted but incubated with a candidate compound. If the time to failure is increased for the candidate compound, the candidate compound is selected and/or identified as a compound capable of reducing muscle fatigue and/or enhancing physical performance, for example in an individual by reducing blood lactate concentration during exercise and/or increasing the blood lactate threshold of an individual for a given work output.

In an additional aspect of the present invention, muscle cells are contacted with a compound and are caused to contract by electrical stimulation at a specific pulse frequency and duration and for a period of time. According to a certain embodiment, the compound is a flavanol such as quercetin, rutin, isoquercetin, isoquercetrin, kaempferol, myricetin, or isohamnetin and sulphate, glucoronide or glycoside conjugated forms thereof. Lactate concentration is measured in the muscle cell culture media. Muscle cells are also contacted with a candidate compound and the muscle cells are caused to contract by electrical stimulation for the same period of time and at the same pulse frequency and duration. Lactate concentration in culture media is then measured and compared with the lactate concentration from cells that were stimulated to contract without compound incubation. The ability of the candidate compound to reduce lactate concentration is assessed as being higher or lower than the ability of the other candidate compounds or a control compound to reduce lactate concentration. In this manner, the capability of a compound to reduce muscle fatigue and/or enhance physical performance, for example in an individual, is determined by reducing blood lactate concentration during exercise and/or increasing the blood lactate threshold of an individual for a given work output.

In a further aspect of the present invention, muscle cells in culture are caused to contract by electrical stimulation to the point of fatigue and eventual failure. The time to failure is measured for quercetin. Muscle cells are also contacted with other candidate compounds. The muscle cells are then caused to contract by electrical stimulation to the point of fatigue and eventual failure. The time to failure for the candidate compound is measured and compared to the time to failure for quercetin or other candidate compounds. If the time to failure for the candidate compound is longer than the time to failure for the comparison compound (quercetin or other candidate compounds), the candidate compound is selected as a compound capable of reducing muscle fatigue and/or enhancing physical performance, for example in an individual by reducing blood lactate concentration during exercise and/or increasing the blood lactate threshold of an individual for a given work output.

BRIEF DESCRIPTION OF THE DRAWINGS

The foregoing and other features and advantages of the present invention will be more fully understood from the following detailed description of illustrative embodiments taken in conjunction with the accompanying drawings. It will be recognized that the results and examples in the figures are only illustrative and other examples and illustrations will be readily recognized by the person of ordinary skill in the art, given the benefit of this disclosure.

DETAILED DESCRIPTION OF CERTAIN EXEMPLARY EMBODIMENTS

Embodiments of the present invention are based on the discovery that certain compounds lower blood lactate concentration in an individual during exercise. Blood lactate concentration is a factor associated with muscle fatigue and muscle failure. According to aspects of the present invention, methods are provided to reduce or lower lactic acid concentration in contracting skeletal muscle. In one embodiment, one or more compounds are administered to muscle cells in a manner to prevent, inhibit, lower and/or reduce lactate concentration in the muscle cell. According to this method of reducing lactic acid in a muscle cell, muscle fatigue is reduced and athletic performance is enhanced.

Compounds within the scope of the present invention that prevent, reduce, inhibit, limit and/or lower the lactic acid concentration in a contracting muscle cell and/or prevent, reduce, inhibit, limit and/or lower the blood lactate concentration in an exercising individual include flavanol compounds such as quercetin, rutin, isoquercetin, isoquercetrin, kaempferol, myricetin, or isohamnetin and sulphate, glucoronide or glycoside conjugated forms thereof. Such compounds include naturally occurring compounds and derivatives and modifications thereof and synthetic compounds. A synthetic compound is generally characterized as any compound created from organic synthesis as oppose to being created by nature.

It is to be understood that embodiments of the present invention include administration of one or more compounds or a plurality of compounds that reduce lactate accumulation from contracting muscle cells within an exercising individual. Further, one or more such compounds or a plurality of such compounds are included in a liquid beverage or food product in amounts sufficient to reduce blood lactate concentration within an exercising individual for a given work output, when administered, delivered or otherwise ingested according to the methods described herein.

According to aspects of the present invention, a compound, such as quercetin, is administered to an individual for a time period before an exercise regimen, including a light exercise regimen, a moderate exercise regimen, a heavy exercise regimen or a competitive athletic event. Time periods within the scope of the present invention include about immediately before the exercise regimen or competitive athletic event, about 5 minutes to about 1 hour before the exercise regimen or competitive athletic event, about 1 to about 5 hours before the exercise regimen or competitive athletic event, about 1 to about 5 days before the exercise regimen or competitive athletic event and about 1 to about 5 weeks before the exercise regimen or competitive athletic event, and any and all ranges and values within the above ranges, whether overlapping or not. The frequency of administration includes administration of the compound about every 30 minutes, about every hour, about every 2-3 hours, about every 3-5 hours, about every 12 hours, about every day, about every 3 days, about every week and the like and any and all ranges and values within the above ranges, whether overlapping or not. The total time period of administration of the compound for a given frequency and amount of the compound before a particular exercise regimen, physical activity or athletic event includes one day or 24 hours, one week, two weeks, three weeks, four weeks, five weeks, six weeks, seven weeks and higher and any and all ranges and values within the above, whether overlapping or not. One of ordinary skill in the art will understand based on the benefit of this disclosure that the amount administered to an individual depends on at least the activity of the compound and its bioavailability in a particular individual. Certain single dose amounts of a compound within the scope of the present invention include between about 1 milligram to about 10 grams, about 5 milligrams to about 5 grams, about 100 milligrams to about 3 grams, about 500 milligrams to about 2 grams and any and all ranges and values within the above ranges, whether overlapping or not. Certain daily dose amounts of a compound within the scope of the present invention include between about 1 milligram to about 10 grams, about 5 milligrams to about 5 grams, about 100 milligrams to about 3 grams, about 500 milligrams to about 2 grams and any and all ranges and values within the above ranges, whether overlapping or not. In a particular embodiment, about 1000 grams of quercetin are administered as a daily dose for about between 25 and about 35 days to an individual before a desired exercise performance, physical activity or athletic event.

Further, certain amounts of a compound within the scope of the present invention include about 1 mg compound per kg of body weight (1 mg/kg) to about 100 mg/kg, about 5 mg/kg to about 50 mg/kg, about 10 mg/kg to about 25 mg/kg, about 15 mg/kg to about 20 mg/kg and any and all ranges and values within the above ranges, whether overlapping or not. According to certain aspect, such an amount is administered in a liquid volume of about 5 to about 30 fluid ounces, about 10 to about 25 fluid ounces, about 15 to about 20 fluid ounces and any and all ranges and values within the above ranges, whether overlapping or not. It is to be understood that frequency of administration may be dependent on the particular compound, the amount of compound or compounds administered, the mode of administration, the ability of the individual to metabolize the compound or compounds and the like. Further, the frequency and amount of compound or compounds administered may be determined by the desired amount of prevention, reduction, inhibition, limitation and/or lowering of lactic acid in muscle cells or blood lactate concentration in an individual during muscle contraction and/or exercise. In general, larger amounts and more frequent administration may more strongly prevent, reduce, inhibit, limit and/or lower the lactic acid concentration in muscle cells or blood lactate concentration in an individual during muscle contraction and/or exercise. Still further, the frequency and amount of compound or compounds administered may also be determined by the desired amount of muscle fatigue reduction and/or improved muscle performance and/or desired increase in blood lactate threshold and/or maximal blood lactate steady state. Individuals desiring to reduce muscle fatigue or improve muscle performance to a greater extent may be more inclined to have greater frequency and higher amounts of compound or compounds administered.

According to aspects of the present invention, the compounds may be administered or delivered to an individual by ingestion by the individual such as by drinking a liquid such as a rehydration or sports beverage or enhanced water or shake, eating solid food products such as food bars, and ingesting eatable film strips, pills, lozenges, chews, gummies, gels, jellies, jellos, pastes, and the like. It is to be understood that the term administration is not limited to the providing of the compound by one individual to another. Instead, the term administration includes an individual providing the compound to herself or himself, such as by drinking a beverage including one or more compounds.

One exemplary route of administration or delivery includes ingestion of the compound or compounds mixed in or otherwise dissolved or suspended in a fluid, such as with an emulsion. It is to be understood that aspects of the present invention include administration of one or more compounds that reduce blood lactate concentration during exercise or a plurality of compounds that reduce blood lactate concentration during exercise. Embodiments of the present invention also include fluids, drinks or beverages including one or more or a plurality of compounds in amounts sufficient to reduce blood lactate concentration during exercise when administered, delivered or otherwise ingested according to the methods described herein. Fluids, drinks and/or beverages within the scope of the present invention include aqueous fluids, such as sports drinks or waters or enhanced waters that may further include one or more beverage ingredients to create a beverage, including carbonated or noncarbonated beverages. As an example, the compound quercetin, alone or in combination with other compounds that reduce blood lactate concentration during exercise, is included in a sports drink, enhanced water or other beverage in an amount sufficient to reduce blood lactate concentration resulting from muscle cell contraction that occurs during muscle contraction such as during exercise regimens or competitive athletic events or other strenuous physical activity, whether the individual is a trained athlete or not. In a particular embodiment, quercetin is present in a sports drink or other beverage and is ingested on a daily basis in a suitable amount and over a suitable number of days prior to a desired exercise, physical activity or athletic event so as to reduce blood lactate concentration during the desired exercise, physical activity or athletic event and to improve muscle and/or exercise and/or physical activity and/or athletic performance.

It should be understood that liquids, sports drinks, rehydration beverages, beverages or other beverage products (all generally referred to as beverages or beverage products) in accordance with this disclosure may have any of numerous different specific formulations or constitutions. The formulation of a beverage product in accordance with this disclosure may vary to a certain extent, depending upon such factors as the product's intended market segment, its desired nutritional characteristics, flavor profile and the like.

Rehydration beverages including one or more compounds, such as quercetin, in an amount sufficient as a daily dosage or as part of a daily dosage may be used in conjunction with physical activity, such as exercise, to replenish fluids and electrolytes lost during the activity as well as to provide additional energy. To this end, rehydration beverages typically comprise at least water, carbohydrates and electrolytes and have a measured osmolality of 250-350 mOsm/kg. The carbohydrates generally included in such beverages are high fructose corn syrup and sucrose. Other rehydration beverages include a carbohydrate blend that undergoes minimal hydrolysis in solution over time, thereby substantially maintaining its initial measured osmolality during storage. Further rehydration/sports beverages, containing such carbohydrate blends, have a low osmolality and are rapidly absorbed by a subject following consumption.

In accordance with one aspect, a carbohydrate blend is provided, which comprises from 35% by weight to 45% by weight fructose and from 55% by weight to 65% by weight glucose. The carbohydrate blend may include a combination of carbohydrates, such as fructose, glucose, sucrose, leucrose, trehalose, galactose, isomaltulose, dextrose, maltodextrin, corn syrup solids and/or glucooligosaccharides and combinations thereof. An aqueous solution containing 6% by weight of the carbohydrate blend has a measured osmolality of 230-300 mOsm/kg. Further, the measured osmolality of the 6% carbohydrate solution does not change by more than 5% during storage for up to six months.

In another aspect, a beverage composition is provided, comprising water and from 4% by weight to 10% by weight of a carbohydrate blend having from 35% by weight to 45% by weight fructose and from 55% by weight to 65% by weight glucose. The beverage may be a rehydration beverage and further include electrolytes, edible acids, vitamins, functional ingredients, coloring agents, flavoring agents and combinations thereof.

In certain embodiments of the carbohydrate blend and beverage composition disclosed here, at least some of the glucose is provided by glucooligosaccharides, which may have a structure containing between about three and seven degrees of saccharide polymerization or up to six degrees of saccharide polymerization, while in other embodiments the structure contains up to ten degrees of saccharide polymerization. In certain embodiments, at least some of the glucose is provided by polysaccharides having a degree of polymerization of eleven degrees and greater. In certain exemplary embodiments of beverage compositions according to this disclosure, a rehydration beverage is provided having a measured osmolality in the range of 230 mOsm/kg to 260 mOsm/kg. In certain embodiments of the present invention, the structure of the glucooligosaccharides included in the carbohydrate blend has an initial α-(1,4) glucose-to-glucose linkage followed by alternating α-(1,3) glucose-to-glucose linkages and α-(1,6) glucose-to-glucose linkages. A suitable glucooligosaccharide is produced by Cargill, Incorporated, Wyzata, Minn., under the name Glucohydrate.

Osmolality is defined as the number of osmoles of solute per kilogram of solvent, where one osmole is provided by each mole of ion charge. Glucooligosaccharides have larger molecular weights than smaller carbohydrates, such as disaccharides or monosaccharides. Accordingly, a first solution of a carbohydrate blend comprising a particular weight percent of glucooligosaccharides would have a lower osmolality than a second carbohydrate solution that is identical except that it instead comprises that particular weight percent of disaccharides in place of the glucooligosaccharides. The reason for this is because fewer total moles of carbohydrate would be present in the first solution than in the second solution. Consequently, whereas rehydration beverages comprising sucrose and high fructose corn syrup (HFCS) typically have an initial measured osmolality of about 330 mOsm/kg, an aqueous solution containing between about 4% by weight and about 10% by weight of the carbohydrate blend has a measured osmolality of about 230-300 mOsm/kg. Further, in certain exemplary embodiments of beverage compositions according to this disclosure, a rehydration beverage composition is provided having a measured osmolality in the range of 230 mOsm/kg to 260 mOsm/kg.

Beverage compositions according to different embodiments may comprise one or more carbohydrate source(s). In certain embodiments, the carbohydrates may include sources of monosaccharides, disaccharides and glucooligosaccharides, while in other embodiments the carbohydrates also include sources of polysaccharides, for example corn syrup solids. In certain embodiments, a beverage composition is provided that comprises water and from 4% by weight to 10% by weight of a carbohydrate blend having from 35% by weight to 45% by weight fructose and from 55% by weight to 65% by weight glucose. At least some of the glucose is provided by glucooligosaccharides. The beverage may be a rehydration beverage and further include electrolytes, edible acids, coloring agents, flavoring agents, vitamins, functional ingredients and combinations thereof.

Advantageously, certain embodiments of the present invention provide compositions, such as rehydration beverage compositions, in which the hydrolysis of the carbohydrate source is minimized. Because hydrolysis of carbohydrates results in an increase of the total number of moles of carbohydrate, the osmolality of compositions that are subjected to hydrolysis will exhibit an increase in measured osmolality over time. In contrast, the measured osmolality of compositions comprising 4% by weight to 10% by weight of a carbohydrate blend according to the present invention does not increase by more than 5% during storage for up to six months. Accordingly, compositions according to embodiments of the invention generally provide rehydration beverages that have a measured osmolality below that of plasma, (e.g., approximately 300 mOsm/kg), and are quickly absorbed by the gastrointestinal system both immediately, and for up to at least six months, following manufacture.

It will generally be an option to add further ingredients to the formulation of a particular beverage embodiment, including sports drinks or rehydration beverages. One or more sweeteners, flavorings, electrolytes, vitamins, fruit juices or other fruit products, tastents, masking agents and the like, flavor enhancers, and/or carbonation typically may be added to any such formulations to vary the taste, mouthfeel, nutritional characteristics, etc. In general, a beverage in accordance with this disclosure typically comprises at least water, one or more lactate lowering compounds in accordance with the present invention, sweetener, acidulant, colorant and/or flavoring It is to be understood that beverage ingredients include both natural and artificial ingredients. Exemplary flavorings which may be suitable for at least certain formulations in accordance with this disclosure include fruit flavoring, cola flavoring, citrus flavoring, spice flavorings and others. Carbonation in the form of carbon dioxide may be added for effervescence. Preservatives may be added if desired, depending upon the other ingredients, production technique, desired shelf life, etc. Optionally, caffeine may be added. Certain exemplary embodiments of the beverages disclosed here are cola-flavored carbonated beverages, characteristically containing carbonated water, sweetener, kola nut extract and/or other flavoring, caramel coloring, phosphoric acid, and optionally other ingredients. Additional and alternative suitable ingredients will be recognized by those skilled in the art given the benefit of this disclosure.

The beverage products disclosed here include beverages, i.e., ready-to-drink liquid formulations, beverage concentrates and the like. As used herein, the term "ready-to-drink" refers to a beverage that can be ingested as-is. That is, the ready-to-drink beverage requires no dilution or additions prior to ingestion by a consumer. Beverage products include, e.g., sports drinks, carbonated and non-carbonated soft drinks, fountain beverages, frozen ready-to-drink beverages, coffee beverages, tea beverages, dairy beverages, powdered soft drinks, as well as liquid concentrates, flavored waters, enhanced waters, fruit juice and fruit juice-flavored drinks, and sport drinks. In a basic form, beverage ingredients include one or more of water, one or more lactate lowering compounds, an edible acid, a flavorant, salts, sweeteners, a colorant, a preservative and mixtures of any of them. In embodiments providing a packaged ready-to-drink beverage, the beverage composition may be pre-mixed with a liquid such as water. In certain embodiments, the ready-to-drink beverage comprises about 80-99 weight percent (wt %) of liquid of the total weight of the beverage. Unless otherwise specified, all weight percentages are based on the total weight of a ready-to-drink beverage. In further embodiments, the beverage composition can be packaged as an edible composition or concentrate, such as a dry mix (e.g., powder) or a liquid concentrate for later reconstitution with one or more liquids to form a beverage. The concentrated composition may be associated with instructions for preparing the beverage composition. In another embodiment, a beverage concentrate may be packaged as gels, capsules, or tablets which are consumed with liquid. When provided in these forms, the beverage composition may comprise instructions to mix or consume with an amount of liquid which is equal to about 80-99 wt % of the prepared beverage composition.

The terms "beverage concentrate," "throw beverage syrup" and "syrup" are used interchangeably throughout this disclosure. As used here "sweetened syrup" is defined as syrup that possesses sweetness, and comprises at least one or more sweeteners. At least certain exemplary embodiments of the beverage concentrates contemplated are prepared with an initial volume of water to which the additional ingredients are added. A single strength beverage composition (i.e., a beverage composition at a concentration that is ready to drink) may be formed from the beverage concentrate or syrup by adding further volumes of water to the concentrate to dilute it to a single strength. Typically, for example, single strength beverages may be prepared from the concentrates by combining approximately 1 part concentrate with between approximately 3 to approximately 7 parts water. In certain exemplary embodiments the single strength beverage is prepared by combining 1 part concentrate with 5 parts water. In certain exemplary embodiments the additional water used to form the single strength beverages is carbonated water. In certain other embodiments, a single strength beverage is directly prepared without the formation of a concentrate and subsequent dilution.

Natural embodiments of the beverage products disclosed here are natural in that they do not contain anything artificial or synthetic (including any color additives regardless of source) that would not normally be expected to be in the food. As used herein, therefore, a "natural" beverage composition is defined in accordance with the following guidelines: Raw materials for a natural ingredient exists or originates in nature. Biological synthesis involving fermentation and enzymes can be employed, but synthesis with chemical reagents is not utilized. Artificial colors, preservatives, and flavors are not considered natural ingredients. Ingredients may be processed or purified through certain specified techniques including at least: physical processes, fermentation, and enzymolysis. Appropriate processes and purification techniques include at least: absorption, adsorption, agglomeration, centrifugation, chopping, cooking (baking, frying, boiling, roasting), cooling, cutting, chromatography, coating, crystallization, digestion, drying (spray, freeze drying, vacuum), evaporation, distillation, electrophoresis, emulsification, encapsulation, extraction, extrusion, filtration, fermentation, grinding, infusion, maceration, microbiological (rennet, enzymes), mixing, peeling, percolation, refrigeration/freezing, squeezing, steeping, washing, heating, mixing, ion exchange, lyophilization, osmose, precipitation, salting out, sublimation, ultrasonic treatment, concentration, flocculation, homogenization, reconstitution, enzymolysis (using enzymes found in nature). Processing aids (currently defined as substances used as manufacturing aids to enhance the appeal or utility of a food component, including clarifying agents, catalysts, flocculants, filter aids, and crystallization inhibitors, etc. See 21 CFR § 170.3(o)(24)) are considered incidental additives and may be used if removed appropriately. Substantially clear embodiments of the beverage products disclosed here are substantially clear in that the beverages have substantially no turbidity and substantially no color.

Water is a basic ingredient in the beverage products disclosed here, typically being the vehicle or primary liquid portion in which the lactate lowering compound is provided and the remaining ingredients are dissolved, emulsified, suspended or dispersed. Purified water can be used in the manufacture of certain embodiments of the beverages disclosed here, and water of a standard beverage quality can be employed in order not to adversely affect beverage taste, odor, or appearance. The water typically will be clear, colorless, free from objectionable minerals, tastes and odors, free from organic matter, low in alkalinity and of acceptable microbiological quality based on industry and government standards applicable at the time of producing the beverage. In certain typical embodiments, water is present at a level of from about 80% to about 99.9% by weight of the beverage. In at least certain exemplary embodiments the water used in beverages and concentrates disclosed here is "treated water," which refers to water that has been treated to reduce the total dissolved solids of the water prior to optional supplementation, e.g., with calcium as disclosed in U.S. Pat. No. 7,052,725. Methods of producing treated water are known to those of ordinary skill in the art and include deionization, distillation, filtration and reverse osmosis ("r-o"), among others. The terms "treated water," "purified water," "demineralized water," "distilled water," and "r-o water" are understood to be generally synonymous in this discussion, referring to water from which substantially all mineral content has been removed, typically containing no more than about 500 ppm total dissolved solids, e.g. 250 ppm total dissolved solids.

In one embodiment, the beverage composition includes an electrolyte source for providing sodium (Na). Sodium may be provided by compounds of sodium, such as sodium chloride, sodium citrate, sodium carbonate, sodium bicarbonate, sodium lactate, trisodium citrate, sodium gluconate, monosodium phosphate, disodium phosphate, trisodium phosphate, tetrasodium acid pyrophosphate, sodium acid sulfate, or combinations thereof. In one embodiment, the sodium is provided by sodium lactate, which is about 20.5% by weight sodium. In another embodiment, the sodium is provided by sodium chloride, which is about 39.4% by weight sodium. In a further embodiment, the sodium is provided by sodium acid sulfate, which is about 19.2% by weight sodium. In yet another embodiment, the sodium is provided by sodium gluconate, which is about 10.5% by weight sodium.

In select beverage embodiments, the amount of sodium is about 0.03% by weight to about 0.06% by weight of the finished product or combinations thereof. In select embodiments, the amount of sodium is about 0.03% by weight to about 0.06% by weight of the beverage. Other amounts may also be useful, depending on the application and other factors. In one embodiment, the sodium is provided by sodium chloride and sodium citrate.

Additional types of electrolyte sources to provide, for example, potassium (K), magnesium (Mg), calcium (Ca) and chloride (Cl) ions can also be included in the beverage composition in addition to or independently of sodium (Na). The different types of electrolytes can be provided by their compounds or a combination of their compounds.

For example, an electrolyte source for providing calcium includes potassium acetate, potassium bicarbonate, potassium bromide, potassium chloride, potassium citrate, potassium-D-gluconate, potassium phosphate such as mono- and dibasic potassium phosphate, tropotassium phosphate, tetrapotassium pyrophosphate, potassium sulfate, potassium acetate, potassium bicarbonate, potassium bromide, tripotassium citrate, calcium acetate, calcium chloride, calcium citrate, calcium-D-gluconate, calcium lactate, calcium laevulinate, dibasic calcium phosphate, magnesium chloride, magnesium carbonate and magnesium sulphate, or a combination thereof.

In certain embodiments, the electrolyte blend includes an electrolyte source for providing chloride (Cl). Chloride may be provided by compounds of chloride, such as magnesium chloride hexahydrate, potassium chloride, sodium chloride, anhydrous calcium chloride, or combinations thereof. In one embodiment, the chloride is provided by potassium chloride, which is about 47.5% by weight chloride. In another embodiment, the chloride is provided by sodium chloride, which is about 60.6% by weight chloride. In a further embodiment, the chloride is provided by calcium chloride (anhydrous), which is about 63.9% by weight chloride. In select beverage embodiments, the amount of chloride is about 0.03% by weight to about 0.06% by weight of the finished product.

In certain embodiments, the electrolyte blend includes an electrolyte source for providing calcium (Ca). Calcium may be provided by compounds of calcium, such as anhydrous calcium chloride, calcium acetate, calcium chloride, calcium citrate, calcium-D-gluconate, calcium lactate, calcium laevulinate, dibasic calcium phosphate. In one embodiment, the calcium is provided by calcium chloride anhydrous, which is about 36.1% by weight calcium. In select beverage embodiments, the amount of calcium is about 0.01% by weight to about 0.03% by weight of the finished product.

Additional types of electrolyte sources to provide, for example, magnesium (Mg) ions, can also be included in the electrolyte blend in addition to or independently of sodium (Na). Different types of electrolytes can be provided by their compounds or a combination of their compounds. For example, the magnesium compounds can include magnesium chloride, magnesium carbonate and magnesium sulfate, or a combination thereof.

In one embodiment of a sports beverage, the potassium ions are provided by monopotassium phosphate. In one such embodiment, monopotassium phosphate comprises around about 0.0435% by weight of the beverage composition. In another embodiment, the beverage may contain about 0.01% by weight to about 0.04% by weight of potassium, about 0.01% by weight to about 0.02% by weight of magnesium, about 0.001% by weight to about 0.003% by weight of calcium, about 0.02% by weight to about 0.03% by weight of chloride. Other amounts or combinations may also be useful.

In one embodiment, the potassium ions are provided by monopotassium phosphate or dipotassium phosphate. In one such embodiment, monopotassium phosphate comprises around about 0.0439% by weight of the beverage composition. In another embodiment, the beverage may contain about 0.01% by weight to about 0.04% by weight of potassium, about 0.01% by weight to about 0.02% by weight of magnesium, about 0.001% by weight to about 0.003% by weight of calcium, about 0.02% by weight to about 0.03% by weight of chloride. Other amounts or combinations may also be useful. It is to be understood that any combination of electrolytes from among those listed above and those known to those of skill in the art and envisioned by the present invention.

An edible acid used in the beverages products disclosed herein may serve any one or more of several functions, including, for example, lending tartness to the taste of the beverage, enhancing palatability, increasing thirst quenching effect, modifying sweetness and acting as a mild preservative. Suitable acids are known and will be apparent to those skilled in the art given the benefit of this disclosure. Exemplary acids suitable for use in some or all embodiments of the beverage products disclosed here include phosphoric acid, citric acid, malic acid, tartaric acid, ascorbic acid, lactic acid, formic acid, fumaric acid, gluconic acid, succinic acid, maleic acid, sodium acid sulfate, adipic acid, cinnamic acid, glutaric acid, and mixtures of any of them. Typically, the acid is phosphoric acid, citric acid, malic acid, or combinations thereof such as phosphoric acid and citric acid.

The acid may be used in solution form, for example, and in an amount sufficient to provide the desired pH of the beverage. The particular acid or acids chosen and the amount used will depend, in part, on the other ingredients, the desired shelf life of the beverage product, as well as effects on the beverage pH, titratable acidity, and taste. Typically, for example, the one or more acids of the acidulant are used in an amount, collectively, of from about 0.01% to about 1.0% by weight of the beverage, e.g., from about 0.01% to about 0.5% by weight, from about 0.05% to about 0.5% by weight, from about 0.05% to about 0.25% by weight, from about 0.1% to about 0.25% by weight, depending upon the acidulant used, desired pH, other ingredients used, etc. The pH of at least certain exemplary embodiments of the beverages disclosed here may be a value within the range of from about 2.0 to 5.0, about 2.5 to 4.0, about 2.8 to 3.3 or about 3.0 to 3.2., e.g., 3.1. The acid in certain exemplary embodiments enhances beverage flavor. Too much acid may impair the beverage flavor and result in tartness or other off-taste, while too little acid may make the beverage taste flat.

Those skilled in the art, given the benefit of this disclosure, will recognize that when preparing beverage products containing sweeteners such as peptide-based artificial sweeteners such as aspartame, the resulting beverage composition is best maintained below a certain pH to retain the sweetening effect of the artificial sweetener. In the formation of calcium-supplemented beverages, the presence of calcium salts increases the pH which requires additional acids to both assist the dissolution of the salt and maintain a desirable pH for stability of the artificial sweetener. The presence of the additional acid in the beverage composition, which increases the titratable acidity of the composition, will result in a more tart or sour taste to the resulting beverage. It will be within the ability of those skilled in the art, given the benefit of this disclosure, to select a suitable acid or combination of acids and the amounts of such acids for the acidulant component of any particular embodiment of the beverage products disclosed here.

Sweeteners may be used in the beverage product disclosed herein. Such sweeteners suitable for use in various exemplary embodiments of beverage products include natural and artificial or synthetic sweeteners. Suitable sweeteners and combinations of sweeteners are selected for the desired nutritional characteristics, taste profile for the beverage, mouthfeel and other organoleptic factors. As used herein, "taste" refers to a combination of sweetness perception, temporal effects of sweetness perception, i.e., on-set and duration, off-tastes, e.g. bitterness and metallic taste, residual perception (aftertaste) and tactile perception, e.g. body and thickness. As used herein, a "full-calorie" beverage formulation is one fully sweetened with a nutritive sweetener. The term "nutritive sweetener" refers generally to sweeteners which provide significant caloric content in typical usage amounts, e.g., more than about 5 calories per 8 oz. serving of beverage. As used herein, a "potent sweetener" means a sweetener which is at least twice as sweet as sugar, that is, a sweetener which on a weight basis requires no more than half the weight of sugar to achieve an equivalent sweetness. For example, a potent sweetener may require less than one-half the weight of sugar to achieve an equivalent sweetness in a beverage sweetened to a level of 10 degrees Brix with sugar. Potent sweeteners include both nutritive (e.g., Lo Han Guo juice concentrate) and non-nutritive sweeteners (e.g., typically, Lo Han Guo powder). In addition, potent sweeteners include both natural potent sweeteners and artificial potent sweeteners. However, for natural beverage products disclosed here, only natural potent sweeteners are employed.

Sweeteners suitable for at least certain exemplary embodiments include, for example, sugar alcohols such as sorbitol, mannitol, xylitol, lactitol, isomalt, and malitol. Other sweeteners include tagatose, e.g., D-tagatose, and combinations of tagatose with the sugar alcohol erythritol.

Exemplary natural nutritive sweeteners suitable for some or all embodiments of the beverage products disclosed here include crystalline or liquid sucrose, fructose, glucose, dextrose, maltose, trehalose, fructo-oligosaccharides, glucose-fructose syrup from natural sources such as apple, chicory, honey, etc., e.g., high fructose corn syrup, invert sugar and the like and mixtures of any of them; exemplary artificial sweeteners suitable for some or all embodiments of the beverages disclosed here include saccharin, cyclamate, aspartame, other dipeptides, acesulfame potassium, and other such potent sweeteners, and mixtures of any of them. Also, in at least certain exemplary embodiments of the beverages disclosed here, combinations of one or more natural nutritive sweeteners, one or more artificial sweeteners and/or one or more natural non-nutritive potent sweeteners are used to provide the sweetness and other aspects of desired taste profile and nutritive characteristics. It should also be recognized that certain such sweeteners will, either in addition or instead, act as tastents, masking agents or the like in various embodiments of the beverages disclosed here, e.g., when used in amounts below its (or their) sweetness perception threshold in the beverage in question.

High-potency sweeteners useful in the beverages of the present invention include one or more of a natural high-potency sweetener such as steviol glycosides, such as rebaudiosides such as rebaudioside A, rebaudioside B, rebaudioside C, rebaudioside D, rebaudioside E, rebaudioside F, dulcoside A, dulcoside B, rubusoside, stevia, stevioside, mogroside IV, mogroside V, Luo Han Guo sweetener, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, cyclocarioside I, and combinations thereof.

Sweeteners suitable for use in various embodiments of the beverages disclosed here include nutritive and non-nutritive, natural and artificial or synthetic sweeteners. Non-nutritive artificial sweeteners suitable for at least certain exemplary embodiments include, for example, peptide based sweeteners, e.g., aspartame, neotame, and alitame, and non-peptide based sweeteners, for example, sodium saccharin, calcium saccharin, acesulfame (including but not limited to acesulfame potassium), cyclamate (including but not limited to sodium cyclamate and/or calcium cyclamate), neohesperidin dihydrochalcone, and sucralose. Alitame may be less desirable for caramel-containing beverages where it has been known to form a precipitate. Other non-nutritive sweeteners suitable for at least certain exemplary embodiments include, for example, glycyrrhizin, neohesperidin dihydrochalcone, maltose, lactose, fructo-oligosaccharides, Lo Han Guo powder, steviol glycosides, e.g., rebaudiosides such as Rebaudioside A, stevioside, etc., xylose, arabinose, isomalt, trehalulose, and ribose, and protein sweeteners such as monatin, thaumatin, monellin, brazzein, L-alanine and glycine related compounds and mixtures of any of them. It will be within the ability of those skilled in the art, given the benefit of this disclosure, to select suitable sweeteners or sweetener combinations for a particular embodiment of the beverage compositions disclosed here.

The sweetener can include a monosaccharide or a disaccharide. A certain degree of purity from contamination by metal cations will be expected. Peptides possessing sweet taste are also permitted. The most commonly employed saccharides include sucrose, fructose, dextrose, maltose and lactose and invert sugar. Mixtures of these sugars can be used. Other natural carbohydrates can be used if less or more sweetness is desired. Other types of natural sweeteners structured from carbon, hydrogen and oxygen, e.g., rebaudioside A, stevioside, Lo Han Guo, mogroside V, monatin, can also be used.

Non-limiting examples of nutritive sweeteners include sucrose, liquid sucrose, fructose, liquid fructose, glucose, liquid glucose, glucose-fructose syrup from natural sources such as apple, chicory, agave, honey, etc., e.g., high fructose corn syrup, chicory syrup, Agave syrup, invert sugar, medium invert sugar, maple syrup, maple sugar, honey, brown sugar molasses, e.g., cane molasses and sugar beet molasses, sorghum syrup, an mixtures of any of them.

Sweeteners are present in at least certain exemplary embodiments in an amount of from about 0.1% to about 20% by weight of the beverage, such as from about 6% to about 16% by weight, depending upon the desired level of sweetness for the beverage. To achieve desired beverage uniformity, texture and taste, in certain exemplary embodiments of the natural beverage products disclosed here, standardized liquid sugars as are commonly employed in the beverage industry can be used. Typically such standardized sweeteners are free of traces of non-sugar solids which could adversely affect the flavor, color or consistency of the beverage.

Certain exemplary embodiments of the beverage products disclosed here also may contain small amounts of alkaline agents to adjust pH. Such agents include, e.g., potassium citrate and sodium citrate. For example, the alkaline agent potassium hydroxide may be used in an amount of from about 0.005 wt. % to about 0.02 wt. % (by weight of the beverage), with an amount of about 0.01% being typical for certain beverages. The amount will depend, of course, on the type of alkaline agents and on the degree to which the pH is to be adjusted.

The beverage products disclosed here optionally contain a flavor composition, for example, natural, non-natural and synthetic fruit flavors, botanical flavors, other flavors, and mixtures thereof. As used here, the term "fruit flavor" refers generally to those flavors derived from the edible reproductive part of a seed plant. Included are both those wherein a sweet pulp is associated with the seed, e.g., banana, tomato, cranberry and the like, and those having a small, fleshy berry. The term berry also is used here to include aggregate fruits, i.e., not "true" berries, but fruit commonly accepted as such. Also included within the term "fruit flavor" are synthetically prepared flavors made to simulate fruit flavors derived from natural sources. Examples of suitable fruit or berry sources include whole berries or portions thereof, berry juice, berry juice concentrates, berry purees and blends thereof, dried berry powders, dried berry juice powders, and the like.

Exemplary fruit flavors include the citrus flavors, e.g., orange, lemon, lime grapefruit, tangerine, mandarin orange, tangelo, and pomelo, and such flavors as apple, grape, cherry, and pineapple flavors and the like, and mixtures thereof. In certain exemplary embodiments the beverage concentrates and beverages comprise a fruit flavor component, e.g., a juice concentrate or juice. As used here, the term "botanical flavor" refers to flavors derived from parts of a plant other than the fruit. As such, botanical flavors may include those flavors derived from essential oils and extracts of nuts, bark, roots and leaves. Also included within the term "botanical flavor" are synthetically prepared flavors made to simulate botanical flavors derived from natural sources. Examples of such flavors include cola flavors, tea flavors, and the like, and mixtures thereof. The flavor component may further comprise a blend of several of the above-mentioned flavors. In certain exemplary embodiments of the beverage concentrates and beverages a cola flavor component is used or a tea flavor component. The particular amount of the flavor component useful for imparting flavor characteristics to the beverages of the present invention will depend upon the flavor(s) selected, the flavor impression desired, and the form of the flavor component. Those skilled in the art, given the benefit of this disclosure, will be readily able to determine the amount of any particular flavor component(s) used to achieve the desired flavor impression.

Juices suitable for use in at least certain exemplary embodiments of the beverage products disclosed here include, e.g., fruit, vegetable and berry juices. Juices may be employed in the present invention in the form of a concentrate, puree, single-strength juice, or other suitable forms. The term "juice" as used here includes single-strength fruit, berry, or vegetable juice, as well as concentrates, purees, milks, and other forms. Multiple different fruit, vegetable and/or berry juices may be combined, optionally along with other flavorings, to generate a beverage having the desired flavor. Examples of suitable juice sources include plum, prune, date, currant, fig, grape, raisin, cranberry, pineapple, peach, banana, apple, pear, guava, apricot, Saskatoon berry, blueberry, plains berry, prairie berry, mulberry, elderberry, Barbados cherry (acerola cherry), choke cherry, date, coconut, olive, raspberry, strawberry, huckleberry, loganberry, currant, dewberry, boysenberry, kiwi, cherry, blackberry, quince, buckthorn, passion fruit, sloe, rowan, gooseberry, pomegranate, persimmon, mango, rhubarb, papaya, litchi, lemon, orange, lime, tangerine, mandarin and grapefruit etc. Numerous additional and alternative juices suitable for use in at least certain exemplary embodiments will be apparent to those skilled in the art given the benefit of this disclosure. In the beverages of the present invention employing juice, juice may be used, for example, at a level of at least about 0.2% by weight of the beverage. In certain exemplary embodiments juice is employed at a level of from about 0.2% to about 40% by weight of the beverage. Typically, juice may be used, if at all, in an amount of from about 1% to about 20% by weight.

Certain such juices which are lighter in color may be included in the formulation of certain exemplary embodiments to adjust the flavor and/or increase the juice content of the beverage without darkening the beverage color. Examples of such juices include apple, pear, pineapple, peach, lemon, lime, orange, apricot, grapefruit, tangerine, rhubarb, cassis, quince, passion fruit, papaya, mango, guava, litchi, kiwi, mandarin, coconut, and banana. Deflavored and decolored juices may be employed if desired.

Other flavorings suitable for use in at least certain exemplary embodiments of the beverage products disclosed here include, e.g., spice flavorings, such as cassia, clove, cinnamon, pepper, ginger, vanilla spice flavorings, cardamom, coriander, root beer, sassafras, ginseng, and others. Numerous additional and alternative flavorings suitable for use in at least certain exemplary embodiments will be apparent to those skilled in the art given the benefit of this disclosure. Flavorings may be in the form of an extract, oleoresin, juice concentrate, bottler's base, or other forms known in the art. In at least certain exemplary embodiments, such spice or other flavors complement that of a juice or juice combination.

The one or more flavorings may be used in the form of an emulsion. A flavoring emulsion may be prepared by mixing some or all of the flavorings together, optionally together with other ingredients of the beverage, and an emulsifying agent. The emulsifying agent may be added with or after the flavorings mixed together. In certain exemplary embodiments the emulsifying agent is water-soluble. Exemplary suitable emulsifying agents include gum acacia, modified starch, carboxymethylcellulose, gum tragacanth, gum ghatti and other suitable gums. Additional suitable emulsifying agents will be apparent to those skilled in the art of beverage formulations, given the benefit of this disclosure. The emulsifier in exemplary embodiments comprises greater than about 3% of the mixture of flavorings and emulsifier. In certain exemplary embodiments the emulsifier is from about 5% to about 30% of the mixture.

Carbon dioxide can be used to provide effervescence to certain exemplary embodiments of the beverages disclosed here. Any of the techniques and carbonating equipment known in the art for carbonating beverages may be employed. Carbon dioxide may enhance the beverage taste and appearance and may aid in safeguarding the beverage purity by inhibiting and destroying objectionable bacteria. In certain embodiments, for example, the beverage has a $CO_2$ level up to about 4.0 volumes carbon dioxide. Typical embodiments may have, for example, from about 0.5 to 5.0 volumes of carbon dioxide. As used here and independent claims, one volume of carbon dioxide is defined as the amount of carbon dioxide absorbed by any given quantity of liquid, e.g., water at 60° F. (16° C.) and one atmospheric pressure. A volume of gas occupies the same space as does the liquid by which it is dissolved. The carbon dioxide content may be selected by those skilled in the art based on the desired level of effervescence and the impact of the carbon dioxide on the taste or mouthfeel of the beverage. The carbonation may be natural or synthetic.

The beverage concentrates and beverages disclosed here may contain additional ingredients including, generally, any of those typically found in beverage formulations. These additional ingredients, for example, may typically be added to a stabilized beverage concentrate. Examples of such additional ingredients include, but are not limited to, caramel and other coloring agents or dyes, antifoaming agents, gums, emulsifiers, tea solids, cloud components, and mineral and non-mineral nutritional supplements.

Examples of non-mineral nutritional supplement ingredients are known to those of ordinary skill in the art and include, for example, vitamins, including Vitamins A, D, E (tocopherol), C (ascorbic acid), B (thiamine), $B_2$ (riboflavin), $B_6$, $B_{12}$, and K, niacin, folic acid, biotin, and combinations thereof. The optional non-mineral nutritional supplements are typically present in amounts generally accepted under good manufacturing practices. Exemplary amounts are between about 1% and about 100% RDV, where such RDV are established. In certain exemplary embodiments the non-mineral nutritional supplement ingredient(s) are present in an amount of from about 5% to about 20% RDV, where established.

Preservatives may be used in at least certain embodiments of the beverages disclosed here. That is, at least certain exemplary embodiments contain an optional dissolved preservative system. Solutions with a pH below 4 and especially those below 3 typically are "microstable," i.e., they resist growth of microorganisms, and so are suitable for longer term storage prior to consumption without the need for further preservatives. However, an additional preservative system may be used if desired. If a preservative system is used, it may be added to the beverage product at any suitable time during production, e.g., in some cases prior to the addition of the sweetener. As used here, the terms "preservation system" or "preservatives" include all suitable preservatives approved for use in food and beverage compositions, including, without limitation, such known chemical preservatives as benzoates, e.g., sodium, calcium, and potassium benzoate, sorbates, e.g., sodium, calcium, and potassium sorbate, citrates, e.g., sodium citrate and potassium citrate, polyphosphates, e.g., sodium hexametaphosphate (SHMP), and mixtures thereof, and antioxidants such as ascorbic acid, EDTA, BHA, BHT, TBHQ, dehydroacetic acid, dimethyldicarbonate, ethoxyquin, heptylparaben, and combinations thereof. Preservatives may be used in amounts not exceeding mandated maximum levels under applicable laws and regulations. The level of preservative used typically is adjusted according to the planned final product pH, as well as an evaluation of the microbiological spoilage potential of the particular beverage formulation. The maximum level employed typically is about 0.05% by weight of the beverage. It will be within the ability of those skilled in the art, given the benefit of this disclosure, to select a suitable preservative or combination of preservatives for beverages according to this disclosure.

According to methods of the present invention, the compound or compounds of the present invention, such as quercetin, is delivered to individuals in a method to reduce lactic acid in contracting muscle cells and/or to reduce blood lactate concentration in exercising individuals. When administered as disclosed herein, the compounds are useful in a method of delaying the onset of muscle fatigue and accordingly improving athletic performance by reducing blood lactate concentration resulting from the process of muscle cell contraction.

Embodiments of the present invention are also directed to a muscle cell culture assay that is used to identify compounds useful in reducing blood lactate concentration during exercise resulting from skeletal muscle cell contraction, as well as, to categorize the ability of compounds to be useful in the methods described herein relative to quercetin. According to this aspect of the present invention, the lactate concentration in media used to culture mature myotubes, refered to herein as muscle cells, is determined in the resting state. Mature myotubes are exposed to electrical pulse stimulation (EPS) whereupon they repeatedly contract. The muscle cells are stimulated to repeatedly contract for a period of time, such as 90 minutes. The muscle cell culture media is then analyzed to determine the lactate concentration. According to an additional aspect, myotubes are pretreated with a compound at a suitable concentration and for a suitable time period, followed by electrical pulse stimulation and then analyzed to determine the lactate concentration in cell culture media. The lactate concentration from muscle cells treated with the compound is compared to the lactate concentration in media from untreated muscle cells. Suitable time periods include between about 30 minutes and about 120 minutes about 60 minutes and 100 minutes, and about 90 minutes. Suitable pulse rates include those which replicate muscle cell contraction during exercise and other pulse rates suitable for generating lactic acid in the muscle cells. Useful pulse frequencies include those between about 0.5 Hz and about 4 Hz, about 1 Hz and about 3 Hz, and any ranges or values in between whether overlapping or not. Useful pulse durations include those between about 2 ms to about 24 ms, about 5 ms to about 20 ms, about 10 ms to about 15 ms and any ranges or value in between whether overlapping or not. Suitable concentrations of a candidate compound range from about 0.001 mM to about 50 mM, about 0.01 mM to about 25 mM, about 0.1 mM to about 10 mM, about 0.5 mM to about 5 mM, about 1 mM and any range or value in between the above ranges whether overlapping or not. A compound that reduces lactate concentration in muscle cell culture media is identified as a compound suitable to reduce blood lactate during exercise and further to reduce muscle fatigue and improve athletic performance. According to certain embodiments, quercetin is an exemplary compound that reduces lactic acid concentration in contracting muscle cells and/or reduces blood lactate concentration during exercise. According to certain embodiments, useful compounds reduce blood lactate concentration for a given work output or exercise regimen by from about 1% to about 30%, from about 5% to about 25%, from about 10% to about 20%, and any range or percentage in between, whether overlapping or not.

The following examples are set forth as being representative of the present invention. These examples are not to be construed as limiting the scope of the invention as these and other equivalent embodiments will be apparent in view of the present disclosure, figures, and accompanying claims.

Example 1

Muscle Cell Assay for Identifying Compounds that Reduce Lactic Acid Concentration Mouse C2C12 myoblasts are purchased from American Type Culture Collection (ATCC; Manassas, Va.) and grown to 90% confluence in high glucose Dubecco's Modified Eagle media (DMEM) with 10% fetal bovine serum (FBS). Myoblasts from the purchased lot are grown in T75 flasks and subcultured >5 times prior to plating in collagen coated six-well plates for experimentation. To induce myotube differentiation FBS containing media is replaced with 2% horse serum containing media or serum free media for 5-7 days. Myoblasts are grown and myotubes are maintained with or without antibiotics in a 37° C., 5% $CO_2$ incubator.

Electrical pulsing is applied to the myotubes using a C-Pace EP Cell Culture Stimulator (IonOptix; Milton, Mass.). Cells are stimulated to visibly and repetitively contract for 90 minutes at a pulse frequency of 0.5 Hz and a pulse duration of 24 ms. Immediately prior to stimulation, day old media is removed and replaced with 5 ml of fresh differentiation media.

Example 2

Muscle Cell Assay with Quercetin

For incubation experiments, differentiated myotubes are pre-treated with quercetin and/or other compounds. Approximately 18 hours prior and again immediately before electrical pulse stimulation, DMEM containing 2% horse serum or serum free media is replaced with the same media containing quercetin or other test compounds at varying concentrations. Samples from media from resting and contracted cells (with and without compound incubation) is analyzed enzymatically for lactate with a modified method of Lowry and Passonneau (A Flexible System of Enzymatic Analysis, pages 194-199, Academic Press, INC. 1972 hereby incorporated by reference in its entirety.)

Example 3

Screening for Candidate Compounds That Reduce Lactic Acid Concentration

Candidate compounds are screened for their ability to reduce lactate concentration in media from contracting cells relative to cells incubated with quercetin and/or relative to cells contacted with one or more other candidate compounds. Differentiated myotubes are pre-treated with the candidate compound, preferably in a water soluble form. Approximately 18 hours prior and again immediately before electrical pulse stimulation, DMEM containing 2% horse serum or serum free media is replaced with the same media containing the candidate compound at a concentration of between about 0.001 mM to about 10 mM.

Electrical pulse stimulation of differentiated myotubes is carried out to produce visible, repetitive contraction of cells. A pulse frequency of 0.5 Hz and duration of 24 ms for 90 minutes is used. The lactate concentration in cell culture media is determined and compared to a control experiment lacking the candidate compound or to an experiment where cells are pretreated with a compound such as quercetin. If the lactate concentration in the cell culture media is reduced in muscle cells contacted with the candidate compound relative to the contracted cells without compound incubation, then the candidate compound is identified as a compound capable of reducing muscle fatigue or improving muscle performance by reducing lactic acid concentration in contracting muscle cells and/or blood lactate concentration in an exercising individual. Also, the ability of the candidate compound to reduce lactic acid or lactate relative to quercetin incubation is determined by comparing the lactate concentration in cell culture media from cells stimulated and contacted with the candidate compound in the assay versus the lactate concentration of cells stimulated and contacted with quercetin in the assay.

Example 4

Enhancing Muscle Performance Using Quercetin By Reducing Blood Lactate Concentration Two tests were performed to determine whether quercetin lowers blood lactate or improves maximal lactate steady state: a $VO_{2PEAK}$ test and an onset of blood lactate accumulation [OBLA] test. These tests were performed in a laboratory maintained at 20-25° C. and 35-40% relative humidity with the participants exercising on a Velotron bicycle trainer (Velotron Pro, RacerMate Inc, Seattle, Wash.) calibrated according to manufacturer's recommendations. $VO_{2PEAK}$ was determined using an incremental multistage cycling protocol: following a 10-min warm-up at 100 W, participants cycled at 150 W for five minutes then power output was increased by 50 W every three minutes until 250 W after which power output was increased by 25 W every minute until volitional exhaustion. Oxygen consumption ($VO_2$) and carbon dioxide production ($VCO_2$) were computed from expiratory gases collected and analyzed with a MOXUS metabolic cart (AEI Technologies, Pittsburgh, Pa.). OBLA was determined on a second occasion, separated from the measurement of $VO_{2PEAK}$ by at least seven days. The participants exercised for 3.5 minute stages at 55, 60, 65, 70, 75, 80, 85, and 90% $VO_{2PEAK}$, and 3-mL blood samples were collected during the final 30 sec of each stage for measuring blood lactate concentration, OBLA was determined using curve fitting techniques and expressed as a percentage of $VO_{2PEAK}$. OBLA was determined before and after 28 days of quercetin supplementation (1000 mg/d) contained in a 2% carbohydrate beverage with electrolytes and vitamins C and B3.

Figure 1:
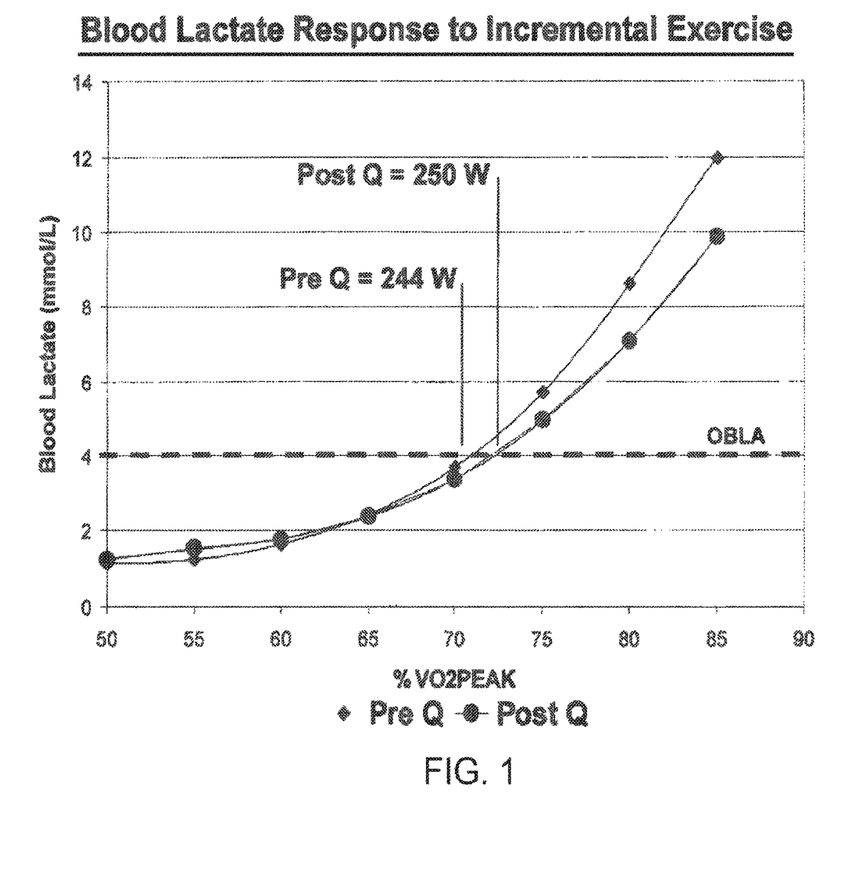
FIG. 1 is a graph plotting blood lactate concentration versus % $VO_2$ Peak showing blood lactate response to incremental exercise in trained cyclists.

FIG. 1 is a graph of blood lactate concentration versus % $VO_2$Peak (oxygen consumption) showing the onset of blood lactate accumulation (OBLA) at 4 mmol/L. The data demonstrates that a higher power output was needed to achieve a 4 mmol blood lactate concentration when quercetin was administered as opposed to when quercetin was not administered, thereby increasing the workload at maximal lactate steady state. The relationship between blood lactate levels and increasing exercise intensity is also depicted in FIG. 1. Normally during exercise, blood lactate levels remain near baseline up to around 60% of maximum effort, after which there is an initial rise and then an exponential rise at near maximal intensities. For most endurance athletes, the exercise intensity that results in a 4 mmol blood lactate concentration (so called onset of blood lactate accumulation or OBLA) is the highest sustainable exercise intensity for a prolonged physical effort (e.g., 1-hour). Therefore, the power output or running velocity during endurance type exercise that elicits a 4 mmol blood lactate is a valid predictor of performance. For example, the higher the power output or running speed to elicit a 4 mmol blood lactate, the faster an athlete will be in finishing a race for a given pace that results in about a 4 mmol blood lactate response. Results from lactate threshold tests conducted on endurance cyclists before and after 28 days of quercetin administration (1000 mg/d) are depicted in FIG. 1 and emphasize that after quercetin supplementation, the cycling power output required to elicit a 4 mmol blood lactate increased by 6 watts (W), from 244 to 250 W which is an advantageous improvement. For example, if a cyclist were able to sustain an average 6 W increase over the duration of a 20 km time trial, the cyclist would finish the course approximately 30 seconds faster.

In addition, FIG. 1 shows that quercetin administration improved the % $VO_2$ Peak where the cyclist achieved a blood lactate concentration of 4 mmol by about 3%. For example, in FIG. 1 it can be seen that the % $VO_2$ Peak to achieve a 4 mmol blood lactate concentration increased from about 71% to about 73% after quercetin administration. Correspondingly, quercetin administration resulted in a decrease in blood lactate concentration at the % $VO_2$ Peak corresponding to a 4 mmol blood lactate concentration without quercetin administration.

Figure 2:
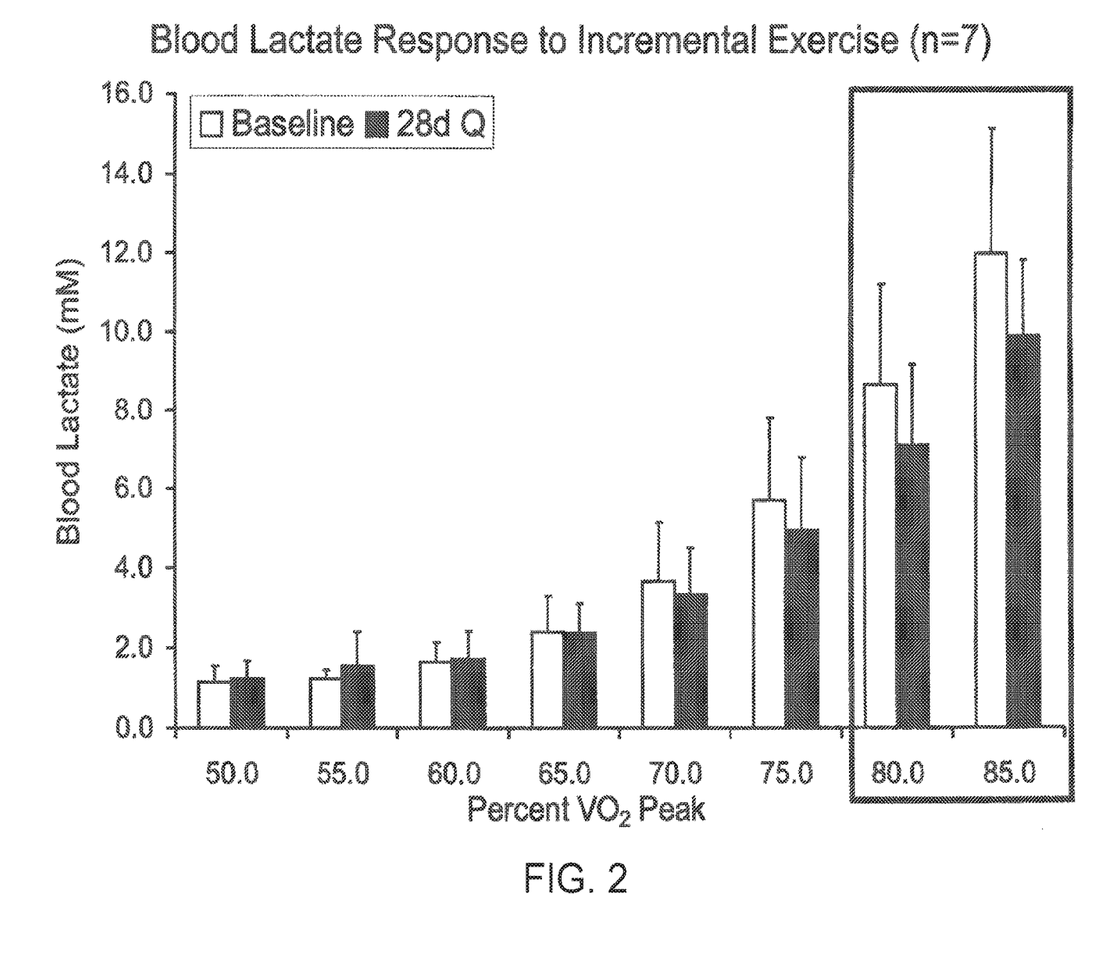
FIG. 2 is a bar graph of blood lactate response to incremental exercise for various % $VO_2$ Peak exercise intensities in trained cyclists showing a reduction in blood lactate at near peak exercise intensity following quercetin administration.

FIG. 2 is a graph of blood lactate response to incremental exercise for various exercise intensities represented as % $VO_2$ Peak. As can be seen in FIG. 2, blood lactate was reduced for a given % $VO_2$ Peak from pre-quercetin administration to post-quercetin administration starting at around 70% of $VO_2$ Peak. Quercetin administration reduced blood lactate concentration in the range of from about 10 to about 17 percent. According to aspects of the present invention, quercetin is administered to reduce blood lactate concentration in an individual for a given % $VO_2$ Peak between about 0.01% to about 30%, between about 0.1% to about 25%, between about 0.5% to about 20%, between about 0.75% to about 10%, between about 0.75% to about 5%, between about 1% to about 5%, between about 1.5% to about 5%, between about 2% to about 5%, between about 2.5% to about 5%, between about 2.5% to about 25%, between about 5.0% to about 20%, between about 7.5% to about 20%, between about 8.0% to about 20%, between about 9.0% to about 20%, between about 10.0% to about 20.0%, between about 10.0% to about 19.0%, between about 10.0% to about 18.0%, between about 10.0% to about 17.0%, and any value or range in between whether overlapping or not.

Example 5

Cell-Based Assay Studies

Figure 3:
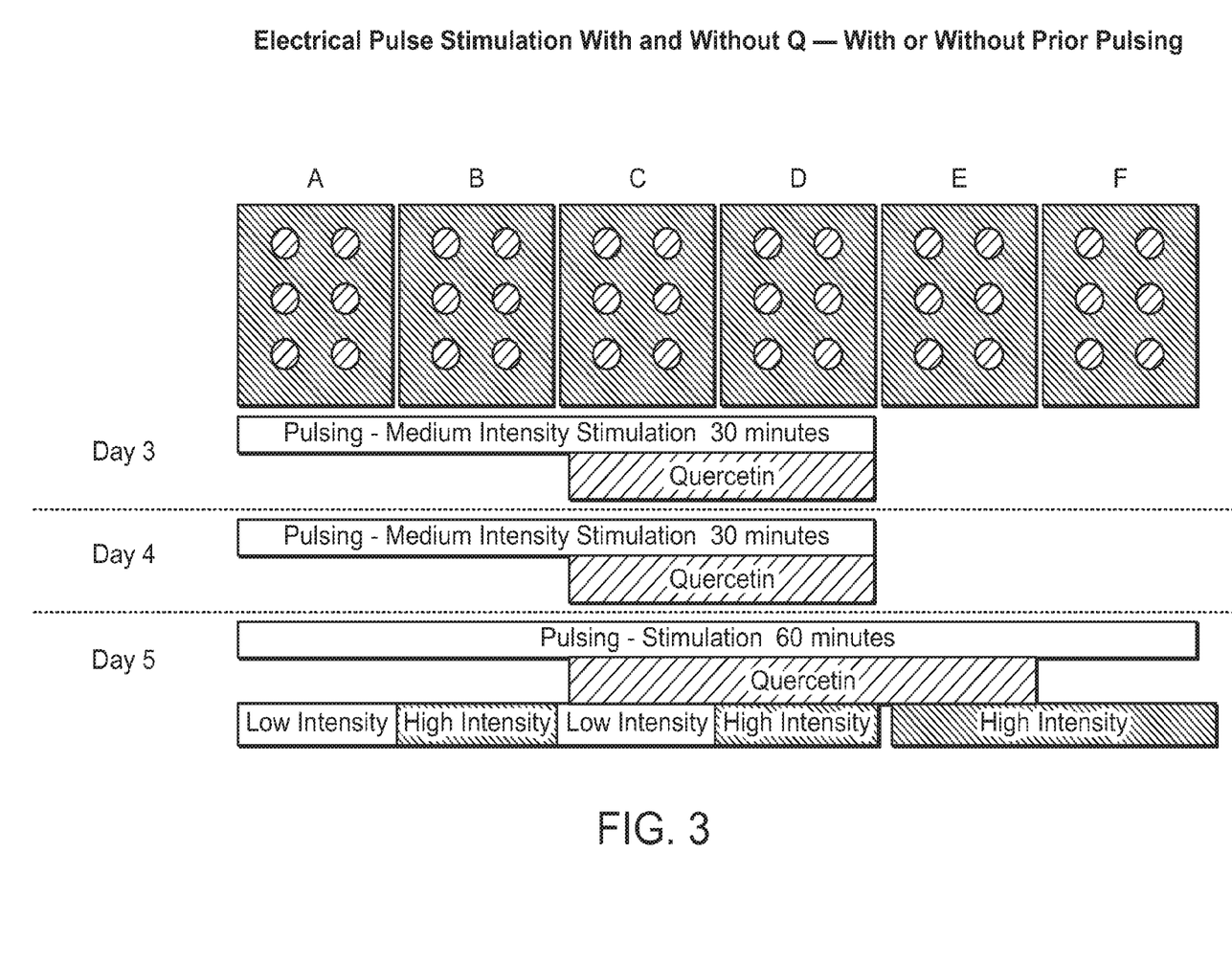
FIG. 3 is a schematic representation of the various electrical pulse stimulation experiments carried out on muscle cells in the presence or absence of quercetin and with or without prior electrical pulse stimulation.

The effect of quercetin on lactate concentration of muscle cells subjected to electrical pulse stimulation as generally described in Example 1 and Example 2 was studied. According to this example and as illustrated in FIG. 3, six 6 well plates (A-F) were seeded with C2C12 cells at a density of 40 k in DMEM growth media for 48 hours. Media was changed every 24 hours. After 48 hours, growth media was replaced with AIM 5 differentiation media which was also changed every 24 hours. Quercetin was added to plates C and D with the change of media 1 hour before the stimulus on days 3 and 4 of differentiation. On days 3 and 4 of differentiation, plates A-D were stimulated for 30 minutes with medium stimulation (10V/2 Hz/12 ms) to simulate training of muscle cells prior to an athletic event. On day 5 of differentiation, the media was changed and quercetin (5 µl of 33 mM stock added to 3 mls of media) was added to plates C, D, and E. After 1-2 hours, 1 ml of media was collected from each plate and stored at −80° C. for future analysis. On day 5 of differentiation, plates A and C were stimulated with low intensity stimulation (10V/0.5 hz/24 ms). Plates B, D, E, and F were stimulated with high intensity stimulation (10V/4 hz/2 ms). 1 ml of media was collected from each plate for future analysis of lactate. For plates E and F, there was no administration of quercetin or electrical pulse stimulation on days 3 and 4 of differentiation. On day 5 of differentiation, plate E was treated with quercetin and subjected to electrical pulse stimulation while plate F was subjected to electrical pulse stimulation but without quercetin administration.

Lactate concentrations were measured with the Enzychrom L-Lactate Kit as follows. A standard was prepared by mixing 200 µl 2.0 mM standard and 800 µl Aim 5 Media to produce 1000 µl 4.0 mM L-lactate Premix. Standards were diluted as follows. 20 µl of each standard were transferred into wells of a clear 96-well plate

| No | Premix + H₂O or Medium | Vol (µL) | L-Lactate (mM) |
|----|------------------------|----------|----------------|
| 1  | 100 µL + 0 µL          | 100      | 4              |
| 2  | 90 L + 10 µL           | 100      | 3.6            |
| 3  | 80 µL + 20 µL          | 100      | 3.2            |
| 4  | 70 µL + 30 µL          | 100      | 2.8            |
| 5  | 60 µL + 40 µL          | 100      | 2.4            |
| 6  | 50 µL + 50 µL          | 100      | 2              |
| 7  | 40 µL + 60 µL          | 100      | 1.6            |
| 8  | 30 µL + 70 µL          | 100      | 1.2            |
| 9  | 20 µL + 80 µL          | 100      | 0.8            |
| 10 | 10 µL + 90 µL          | 100      | 0.4            |
| 11 | 5 µL + 95 µL           | 100      | 0.2            |
| 12 | 0 µL + 100 µL          | 100      | 0              |

For each reaction well, working reagent was prepared by mixing 60 µl Assay Buffer, 1 µl Enzyme A, 1 µl Enzyme B, 10 µl NAD and 14 µl MTT. For the No Enzyme A sample control, the working reagent included 60 µl Assay Buffer, 1 µl Enzyme B, 10 µl NAD and 14 µl MTT. 80 µl of working reagent was added to each well quickly. The plate was tapped to mix briefly and thoroughly. The optical density ($OD_0$) was read for time "zero" at 565 nm and $OD_{20}$ after a 30 minute incubation at room temperature.

Figure 4:
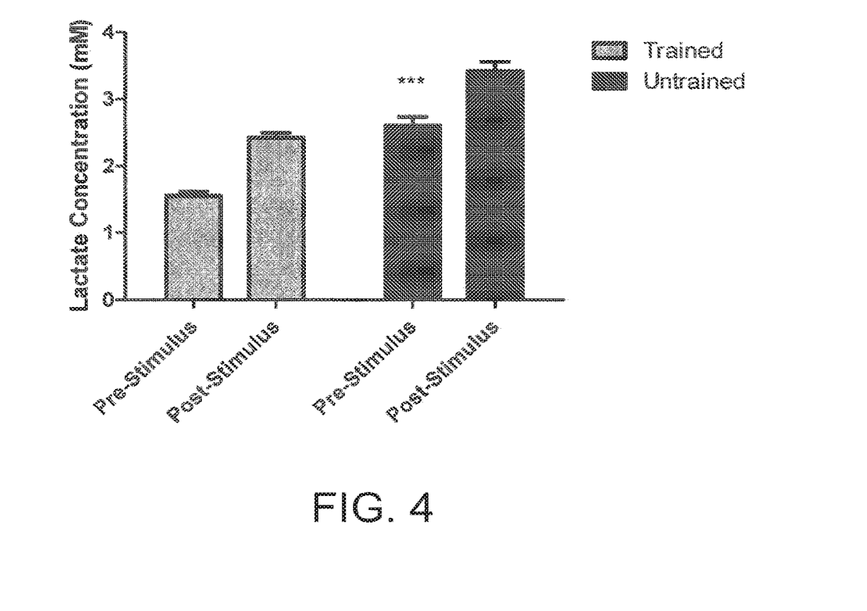
FIG. 4 is a graph of lactate concentration in C2C12 cells without quercetin administration pre and post exercise intensity stimulus with training by electrical stimulus and without training by electrical stimulus.

FIG. 4 is a graph of lactate concentration in C2C12 cells without quercetin administration pre and post exercise intensity stimulus with training by electrical stimulus and without training by electrical stimulus. As FIG. 4 shows, the cells with training had a lower lactate concentration pre and post stimulus compared to cells without training.

Figure 5:
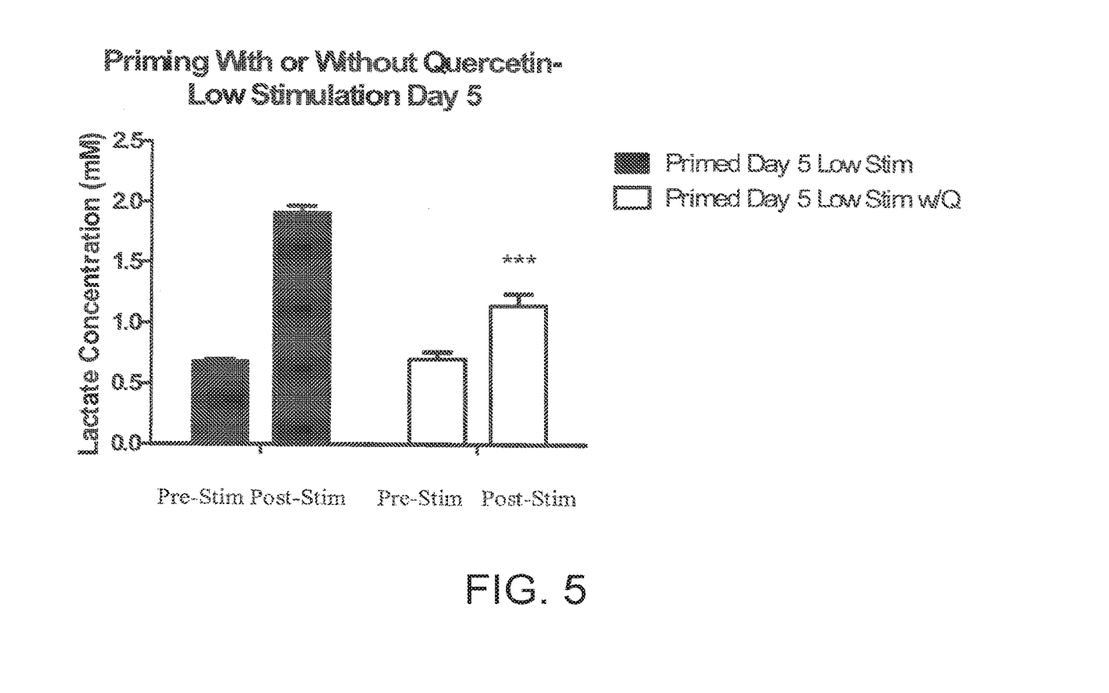
FIG. 5 is a graph of the lactate concentration for plate A (Primed Day 5 Low Stim) and plate C (Primed Day 5 Low Stim w/Q).

FIG. 5 is a graph of the lactate concentration for plate A (Primed Day 5 Low Stim) and plate C (Primed Day 5 Low Stim w/Q). Both plate A and plate C underwent training with medium intensity electrical stimulation for 30 minutes on day 3 and day 4 of differentiation. Quercetin was added before stimulation to plate C on day 3 and day 4 of differentiation. On day 5 of differentiation, quercetin was added to plate C. Lactate concentration was measured pre stimulus for plate A and plate C. The cells were then subjected for 60 minutes to low intensity electrical stimulation and the lactate concentration was measured for plate A and plate C. The results in FIG. 5 show lower day 5 lactate concentration post stimulus for the cells administered with quercetin in plate C on days 3, 4, and 5 compared to the cells in plate A which were not administered quercetin.

Figure 6:
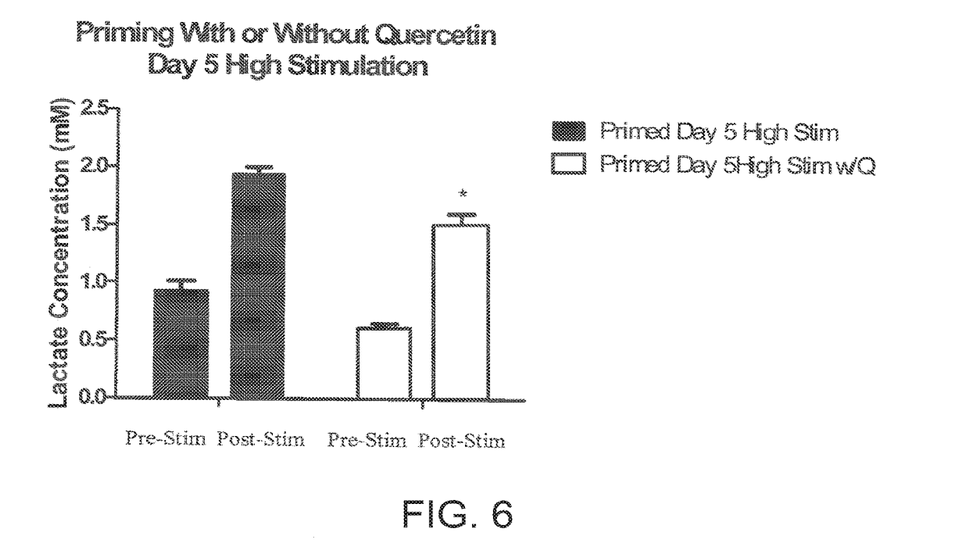
FIG. 6 is a graph of the lactate concentration for plate B (Primed Day 5 High Stim) and plate D (Primed Day 5 High Stim w/Q).

FIG. 6 is a graph of the lactate concentration for plate B (Primed Day 5 High Stim) and plate D (Primed Day 5 High Stim w/Q). Both plate B and plate D underwent training with medium intensity electrical stimulation for 30 minutes on day 3 and day 4 of differentiation. Quercetin was added before stimulation to plate D on day 3 and day 4 of differentiation. On day 5 of differentiation, quercetin was added to plate D. Lactate concentration was measured pre stimulus for plate B and plate D. The cells were then subjected for 60 minutes to high intensity electrical stimulation and the lactate concentration was measured for plate B and plate D. The results in FIG. 6 show lower day 5 lactate concentration post stimulus for the cells administered with quercetin in plate D on days 3, 4, and 5 compared to the cells in plate B which were not administered quercetin.

Figure 7:
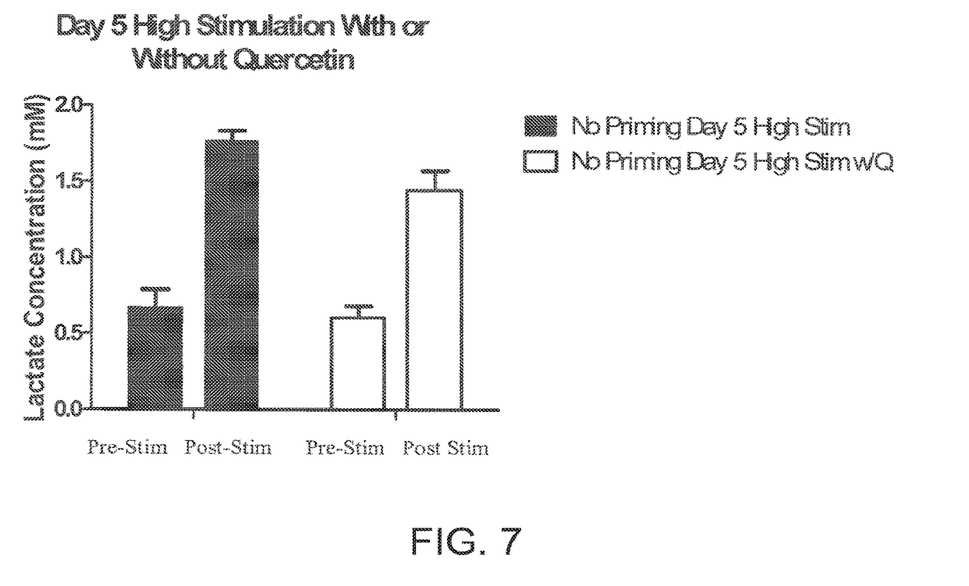
FIG. 7 FIG. 7 is a graph of the lactate concentration for plate E (No Priming Day 5 High Stim w/Q) and plate F (No Priming Day 5 High Stim).

FIG. 7 is a graph of the lactate concentration for plate E (No Priming Day 5 High Stim w/Q) and plate F (No Priming Day 5 High Stim). Neither plate B nor plate D underwent training or were administered quercetin on day 3 and day 4 of differentiation. On day 5 of differentiation, quercetin was added to plate E. Lactate concentration was measured pre stimulus for plate E and plate F. The cells were then subjected for 60 minutes to high intensity electrical stimulation and the lactate concentration was measured for plate E and plate F. The results in FIG. 7 show lower day 5 lactate concentration post stimulus for the cells administered with quercetin in plate E compared to the cells in plate F which were not administered quercetin.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. While the invention has been illustrated and described in detail in the drawings and foregoing description, such illustration and description is to be considered as exemplary and not restrictive in character, it being understood that, only the preferred embodiments have been shown and described and that all changes and modifications that come within the spirit of the invention are desired to be protected. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

What is claimed is:

1. A beverage comprising:
    water;
    a carbohydrate blend comprising from 35 to 45 wt. % fructose and from 5 to 65 wt. % glucose; and
    at least one compound selected from the group consisting of:
    (1) quercetin;
    (2) rutin;
    (3) isoquercetin;
    (4) isoquercetrin;
    (5) kaempferol;
    (6) myricetin;
    (7) isohamnetin;
    (8) sulphate conjugated forms of each of quercetin, rutin, isoquercetin, isoquercetrin, kaempferol, myricetin and isohamnetin;
    (9) glucoronide conjugated forms of each of quercetin, rutin, isoquercetin, isoquercetrin, kaempferol, myricetin and isohamnetin; and
    (10) glycoside conjugated forms of each of quercetin, rutin, isoquercetin, isoquercetrin, kaempferol, myricetin and isohamnetin;
    wherein the at least one compound is present at 500 milligrams to 2 grams.

2. The beverage of claim 1, wherein the at least one compound is present in the beverage in an amount effective to reduce blood lactate concentration in an individual during exercise of the individual when administered to the individual according to a regimen prior to the individual being engaged in the exercise.

3. The beverage of claim 1, wherein the beverage comprises 5 fluid ounces to 30 fluid ounces of water.

4. The beverage of claim 3, wherein the beverage comprises an osmolality of 230-300 mOsm/kg.

5. The beverage of claim 1, wherein the carbohydrate blend provides from 4 wt. % to 10 wt. % of the beverage.

6. The beverage of claim 4, wherein, after storing the beverage for six months, a final storage osmolality of the beverage does not differ from an initial storage osmolality by more than 5% of the initial storage osmolality, wherein the initial storage osmolality is measured at the beginning of the six months and wherein the final storage osmolality is measured at the end of the six months.

7. The beverage of claim 1, wherein the carbohydrate blend comprises glucooligosaccharides.

8. The beverage of claim 7, wherein the glucooligosaccharides have a structure containing up to ten degrees of saccharide polymerization.

9. The beverage of claim 7, wherein the glucooligosaccharides have an initial α-(1,4) glucose-to-glucose linkage followed by alternating α-(1,3) glucose-to-glucose linkages and α-(1,6) glucose-to-glucose linkages.

10. The beverage of claim 8, wherein the glucooligosaccharides have a structure containing up to six degrees of saccharide polymerization.

11. The beverage of claim 8, wherein the glucooligosaccharides have a structure containing three to seven degrees of saccharide polymerization.

12. The beverage of claim 1, wherein the beverage comprises at least 80 wt. % water.

13. The beverage of claim 1, wherein the beverage comprises electrolytes.

14. The beverage of claim 1, further comprising:
the at least one compound in an amount effective to achieve a lower blood lactate concentration in an individual during exercise than would be present in the absence of administering the at least one compound.

15. The beverage of claim 1, wherein the quercetin is present in an amount effective to reduce the blood lactate concentration in an individual for a given % $VO_2$ Peak by 0.01% to 30%.

16. The beverage of claim 1, wherein the quercetin is present in an amount effective to reduce the blood lactate concentration in an individual for a given % $VO_2$ Peak by 10% to 30%.

17. The beverage of claim 1, wherein the at least one compound is present in an amount effective to increase % $VO_2$ Peak at which an individual achieves a blood lactate concentration of 4 mmol/L.

18. The beverage of claim 1, wherein the at least one compound is present in an effective amount, wherein, after an individual receives the effective amount once per day for 28 consecutive days, the effective amount is effective to increase % $VO_2$ Peak at which the individual achieves a blood lactate concentration of 4 mmol/L.

19. The beverage of claim 9, wherein the beverage comprises an osmolality of 250-350 mOsm/kg.

20. A concentrated composition to which liquid is added to form the beverage of claim 1.

21. A concentrated composition to which liquid is added to form a beverage, said concentrated composition comprising:
a carbohydrate blend comprising from 35 to 45 wt. % fructose and from 5 to 65 wt. % glucose; and
at least one compound selected from the group consisting of:
(1) quercetin;
(2) rutin;
(3) isoquercetin;
(4) isoquercetrin;
(5) kaempferol;
(6) myricetin;
(7) isohamnetin;
(8) sulphate conjugated forms of each of quercetin, rutin, isoquercetin, isoquercetrin, kaempferol, myricetin and isohamnetin;
(9) glucoronide conjugated forms of each of quercetin, rutin, isoquercetin, isoquercetrin, kaempferol, myricetin and isohamnetin; and
(10) glycoside conjugated forms of each of quercetin, rutin, isoquercetin, isoquercetrin, kaempferol, myricetin and isohamnetin;
wherein the concentrated composition provides the beverage with 500 milligrams to 2 grams of the at least one compound.

* * * * *